United States Patent
Pillarisetty et al.

(10) Patent No.: US 11,200,966 B2
(45) Date of Patent: Dec. 14, 2021

(54) HEALTHCARE SYSTEM BASED ON DEVICES AND WEARABLES

(71) Applicant: CERNER INNOVATION, INC., Kansas City, KS (US)

(72) Inventors: Satya Krishna Pillarisetty, Bangalore (IN); Krishna Kumar, Bangalore (IN); Mahesh Vilas Kotekar, Bangalore (IN); Pradeep Premakumar, Bangalore (IN); Thampuraj Dharmamoorthy, Bangalore (IN)

(73) Assignee: CERNER INNOVATION, INC., Kansas City, KS (US)

( * ) Notice: Subject to any disclaimer, the term of this patent is extended or adjusted under 35 U.S.C. 154(b) by 590 days.

(21) Appl. No.: 15/392,720

(22) Filed: Dec. 28, 2016

(65) Prior Publication Data

US 2018/0181714 A1 Jun. 28, 2018

Related U.S. Application Data

(63) Continuation-in-part of application No. 15/391,552, filed on Dec. 27, 2016.

(51) Int. Cl.
*G16H 10/60* (2018.01)
*G16H 50/30* (2018.01)

(52) U.S. Cl.
CPC .............. *G16H 10/60* (2018.01); *G16H 50/30* (2018.01)

(58) Field of Classification Search
CPC combination set(s) only.
See application file for complete search history.

(56) References Cited

U.S. PATENT DOCUMENTS 7,860,725 B2 * 12/2010 Gopinathan et al.
2006/0036619 A1 * 2/2006 Fuerst et al.
(Continued)

FOREIGN PATENT DOCUMENTS

WO WO 2006/039944 A1 * 4/2006

OTHER PUBLICATIONS

Preinterview First Office Action received for U.S. Appl. No. 15/391,552, dated Mar. 21, 2019, 11 pages.
(Continued)

*Primary Examiner* — Michael Tomaszewski
*Assistant Examiner* — William T. Monticello
(74) *Attorney, Agent, or Firm* — Shook Hardy & Bacon LLP

(57) ABSTRACT

A computerized method is presented for improving medical records of an individual based on received information from a device or wearable, the method comprising: retrieving from a record-keeping database medical-related information associated with the individual; retrieving from a device associated with the individual a measurable factor; determining, based at least partly on the medical-related information, that the measurable factor poses a medical risk to the individual; and communicating instructions to the record-keeping database to store, in association with the individual, information related to the medical risk. Other methods may associate a location with a medical risk. Other methods may aggregate medical information received from devices or wearables and associate it with a location. Mapping this information with regard to locations may allow early prediction of an epidemic.

19 Claims, 9 Drawing Sheets

(56) References Cited

U.S. PATENT DOCUMENTS

| | | | |
|---|---|---|---|
| 2007/0118399 | A1 | 5/2007 | Avinash et al. |
| 2012/0084092 | A1* | 4/2012 | Kozuch et al. |
| 2012/0158431 | A1* | 6/2012 | Balasubramaniam |
| 2016/0019813 | A1* | 1/2016 | Mullen |
| 2016/0071432 | A1* | 3/2016 | Kurowski et al. |
| 2016/0321395 | A1* | 11/2016 | Colby et al. |
| 2017/0199979 | A1* | 7/2017 | Reiner |
| 2017/0242970 | A1* | 8/2017 | Fink et al. |
| 2017/0286622 | A1 | 10/2017 | Cox et al. |
| 2018/0052970 | A1* | 2/2018 | Boss et al. |
| 2018/0089976 | A1* | 3/2018 | Yarlagadda et al. |
| 2018/0101655 | A1* | 4/2018 | Fogelberg et al. |
| 2018/0101657 | A1 | 4/2018 | Kochura et al. |
| 2018/0144092 | A1* | 5/2018 | Flitsch et al. |

OTHER PUBLICATIONS

Final Office Action received for U.S. Appl. No. 15/391,552, dated Dec. 23, 2019, 19 pages.
Non-Final Office Action received for U.S. Appl. No. 15/391,552, dated Sep. 21, 2020, 16 Pages.
Final Office Action received for U.S. Appl. No. 15/391,552, dated Oct. 7, 2021, 28 pages.

* cited by examiner

HEALTHCARE SYSTEM BASED ON DEVICES AND WEARABLES

CROSS-REFERENCE TO RELATED APPLICATIONS

This application is a continuation-in-part of U.S. application Ser. No. 15/391,552 filed Dec. 27, 2016, entitled "Location-Based Healthcare System," which is hereby incorporated by reference in its entirety.

BACKGROUND

The largest drivers of healthcare cost are over diagnosis and over treatment. Patients are receiving care that is sometimes ineffective and sometimes unsafe. But the truth is that many of the tests and procedures ordered by medical practitioners are wasteful, unnecessary, and potentially harmful. A missing link in treatment or care delivery can be the cause of over diagnosis, which is both economically and physically harmful to a patient. Part of the problem is that in many cases, physicians don't feel clinically certain about what's occurring with the patient, and they're not willing to rest with that uncertainty. Thus, physicians feel that they need to do more tests and refer patients to specialists.

According to studies, environmental factors are a root cause of over diagnosis and cost—particularly in developing countries. Patient exposure to environmental or occupational hazards can set off predisposed ailments or create entirely new ailments, and is a primary concern in preventative healthcare. Environmental impacts are estimated to cause about 25% of death and disease globally, and could reach nearly 35%. It is estimated that one-fifth of the healthcare budget is being consumed by tests and procedures ordered by medical practitioners in trying to identify conditions that are set off by environmental or ecosystem interaction.

There is currently no mechanism that facilitates preventative healthcare based on patient locations to assist physicians in diagnosing the cause of a patient's conditions or ailments that may be associated with environmental factors. Furthermore, there is no healthcare system that may monitor a patient's environmental surroundings on or a patient's clinically significant information, where the surroundings and clinically significant information are monitored from devices and wearables that may be associated with the patient. A location-based system that monitors exposure to certain environmental factors, determines clinically significant information about the patient over time, and assesses patient risk based on this data in light of a patient's medical information or health records would assist physicians in diagnosing particular ailments and reduce inappropriate diagnostic procedures, ultimately promoting decision accuracy and diagnosis for better care delivery. Furthermore, a location-based healthcare system, by aggregating data from multiple patients in a given location, would be capable of predicting an outbreak with greater accuracy and in less time than current measures of physician communication and centralized databases.

BRIEF SUMMARY

The present application generally relates to media, systems, and methods for various embodiments of a method for improving medical records of a patient based on received information from a wearable device. In some embodiments the method may comprise retrieving from an EMR database medical information associated with the patient; retrieving from the wearable device associated with the patient a measurable factor; determining, based at least partly on the medical information, that the measurable factor poses a medical risk to the patient; and communicating instructions to the EMR database to store, in association with the individual, information related to the medical risk. In some embodiments, the patient or others may be alerted that the patient is exposed to the medical risk.

Another embodiment of the present application may be related to a method for tracking location exposure of a patient to factors that may cause a medical risk to the patient. In some embodiments, the method may comprise receiving from a wearable device a measurable factor about the patient or the patient's environment; determining the location of the individual from the mobile device, and associating the measurable factor with the location of the patient when the measurable factor is measured by the wearable; retrieving, from an EMR database, medical-related information associated with the patient; determining, based at least partly on the medical-related information and the measurable factor, that the location poses a medical risk to the individual; and communicating to the EMR database instructions to store information related to the medical risk and the location. Other embodiments may also comprise alerting the patient that the area poses a medical risk. The patient may be alerted to increase or alter preventative medication or be instructed to move from one location to another where the device no longer detects the measurable factor that creates the risk. And yet in other embodiments, the system may aggregate measurable factors from multiple patients or individuals and map according to location, from which a potential outbreak may be detected in its early stages.

Additional objects, advantages, and novel features of the various embodiments are described below.

BRIEF DESCRIPTION OF THE DRAWINGS

The present application is described in detail below with reference to the attached drawing figures, wherein.

DETAILED DESCRIPTION

The subject matter of the present application is described with specificity herein to meet statutory requirements. However, the description itself is not intended to limit the scope of this patent. Rather, the claimed subject matter might also be embodied in other ways, to include different steps or combinations of steps similar to the ones described in this document, in conjunction with other present or future technologies. Moreover, although the term "step" may be used to connote different elements of methods employed, the terms should not be interpreted as implying any particular order among or between various steps unless it explicitly described that the order of the steps is critical for implementing an embodiment.

Various embodiments of the present invention are directed to methods, systems, and computer-readable media for a system and method for improving the healthcare records of a patient by storing patient location information and hazardous exposure that may be associated with medical risks. Some embodiments alert or warn a patient of a medical-related risk associated with an area. Some embodiments provide physicians or medical providers with alerts or recommendations for orders or suggested care associated with patient aliments or symptoms based on exposure to a location-specific contagion. Some embodiments provide instructions to store information related to location-specific exposure to certain environmental events on a health-records database associated with a patient. Other embodiments may determine, based on an aggregate of patient information, that a particular ailment or contagion is increasing in a particular area, and it may provide for an alert to others in the area or other entities of a potential endemic.

Figure 1:
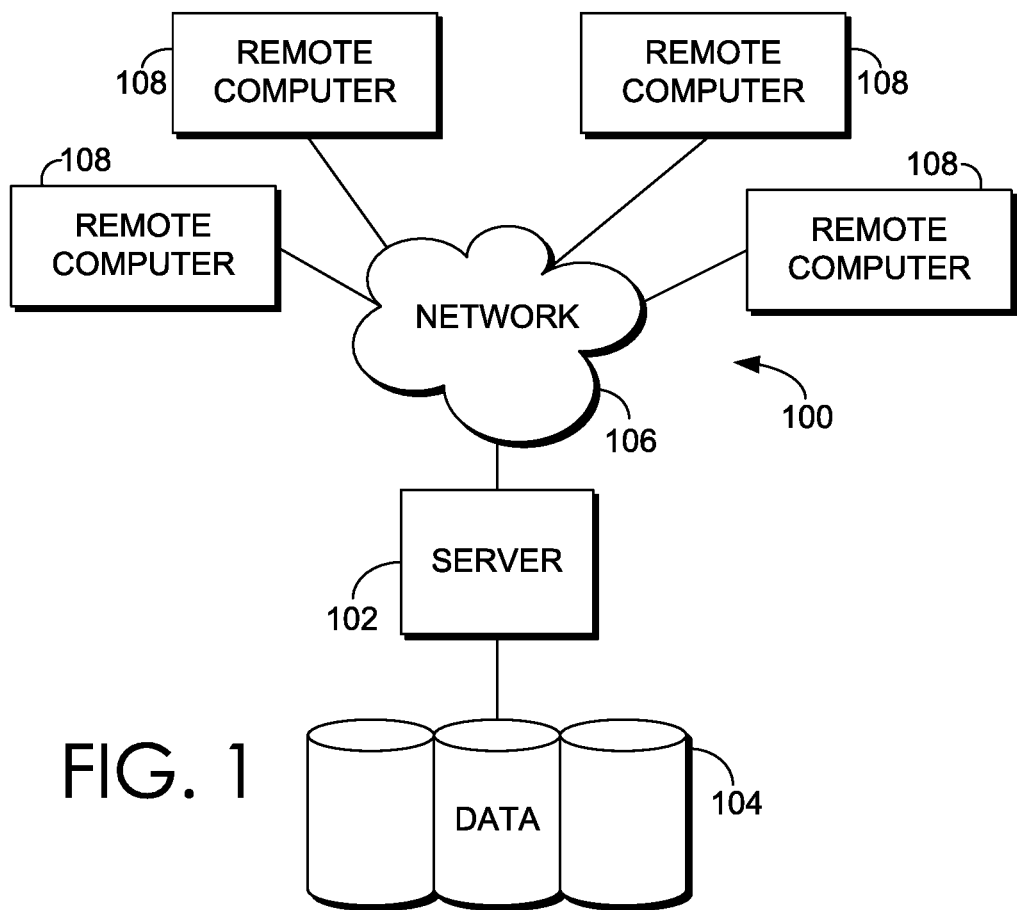
FIG. 1 is a block diagram of an exemplary computing environment suitable to implement embodiments of the various embodiments.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention is a special computing system that can leverage well-known computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of non-transitory computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a microphone (e.g., voice inputs), a touch screen, a pointing device (commonly referred to as a mouse), a trackball, or a touch pad. Other input devices comprise satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
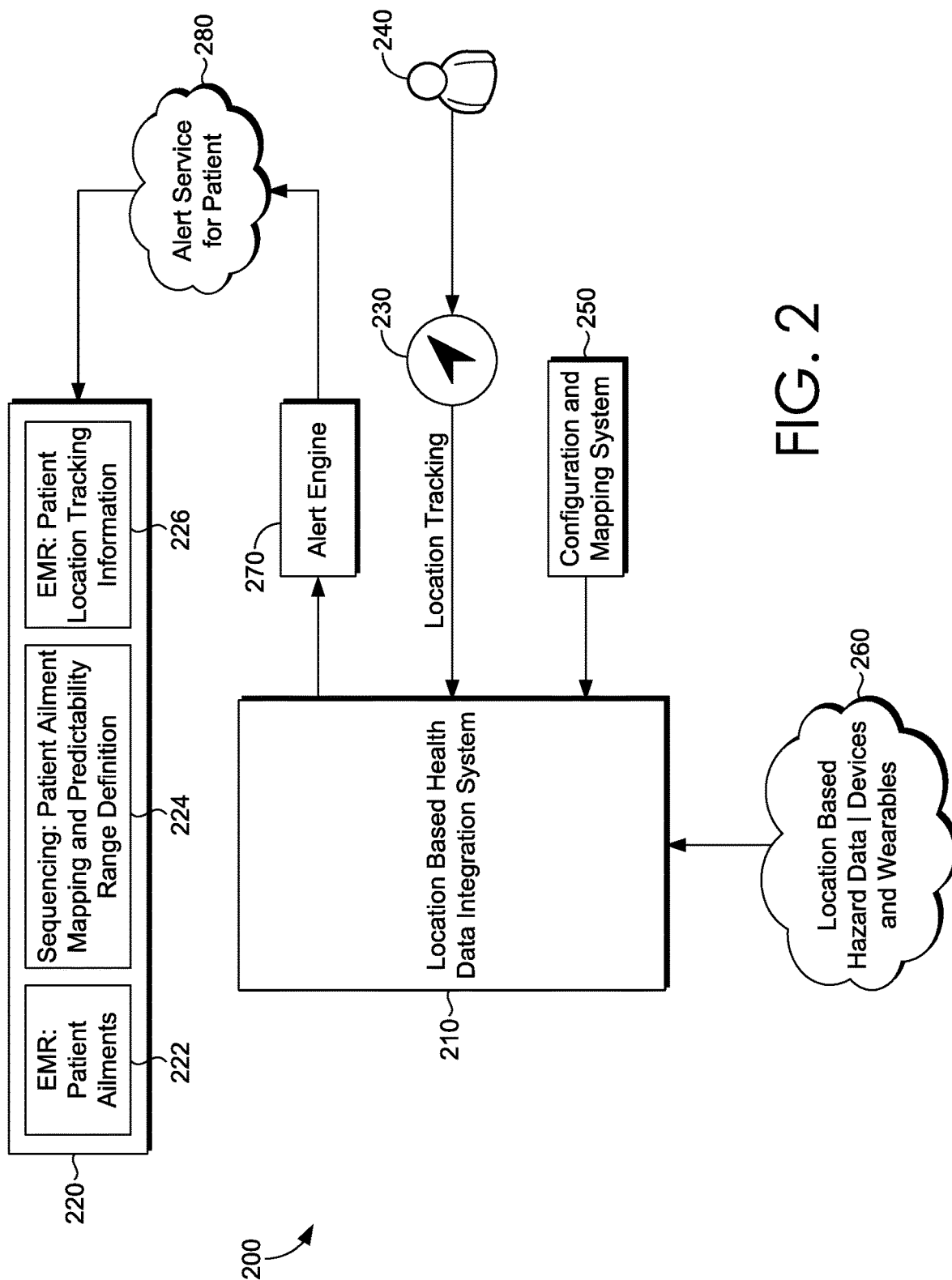
FIG. 2 is a high-level block diagram of an exemplary location-based health system.

Turning now to FIG. 2, a high-level flow chart describing one embodiment of a location-based health system 200 is presented. As shown in this embodiment, the location-based health system 200 may comprise a Location-Based Health Data Integration System (LBHDIS) 210. The LBHDIS 210 may be in communication with a location tracking device 230, which monitors the location of the patient 240. In addition, the LBHDIS 210 may also communicate with other application programming interface (API) services, devices, and wearables 260. The LBHDIS 210 may communicate with an alert engine 270. In some embodiments, the alert engine 270 uses defined rules and categories of various alerts generated from the LBHDIS 260. The alert engine 270 may communicate with an alert service 280. Both the alert service 280 and the LBHDIS 210 may communicate with an electronic medical record (EMR) system 220. The EMR system 220, in some embodiments, may comprise information associated with patient ailments 222; patient genomic sequencing, patient aliment mapping, and predictability range definition 224; and/or patient location tracking information 226.

Figure 3:
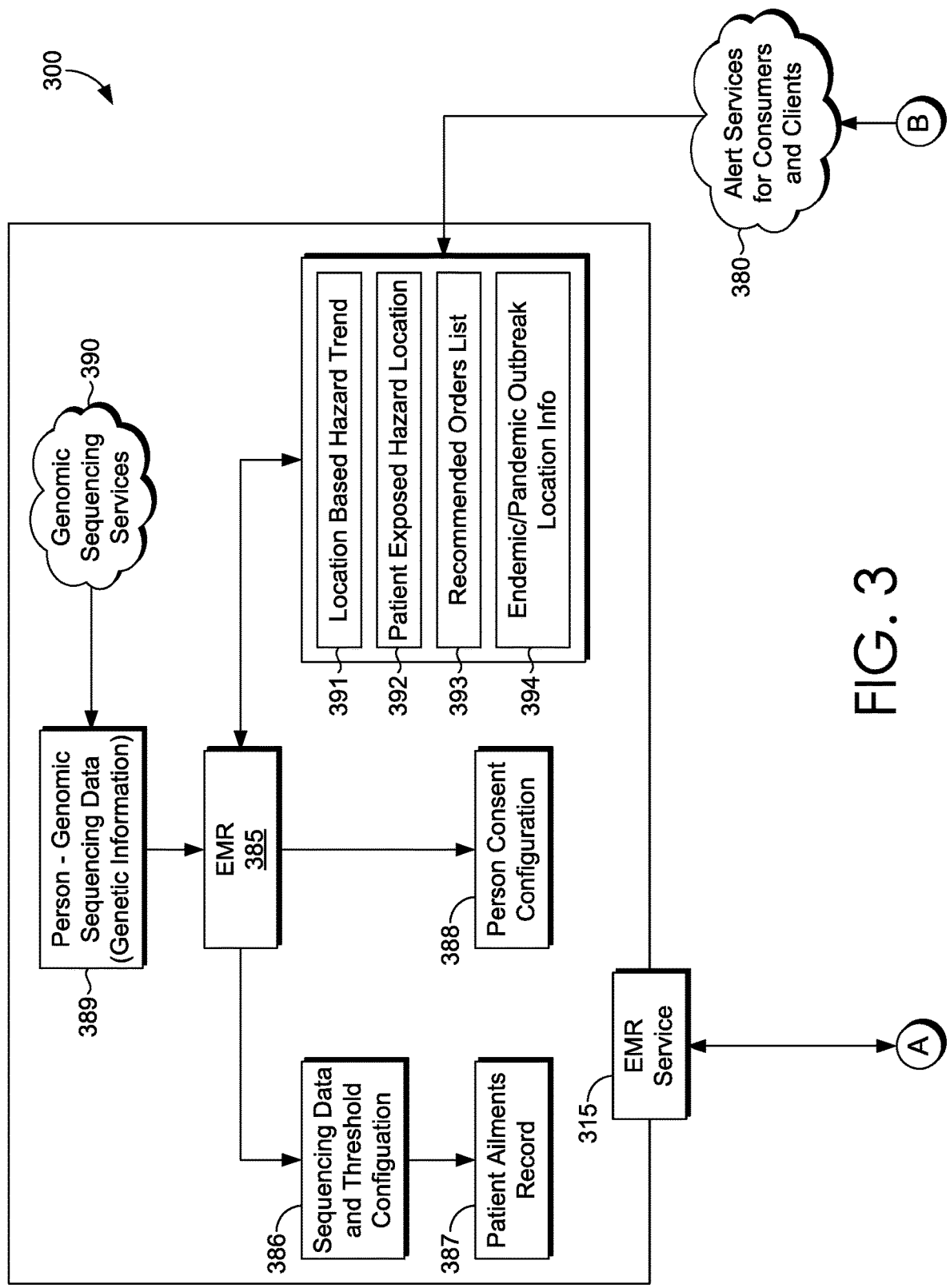
FIG. 3 is a block diagram of an exemplary location-based health system.
Figure 3:
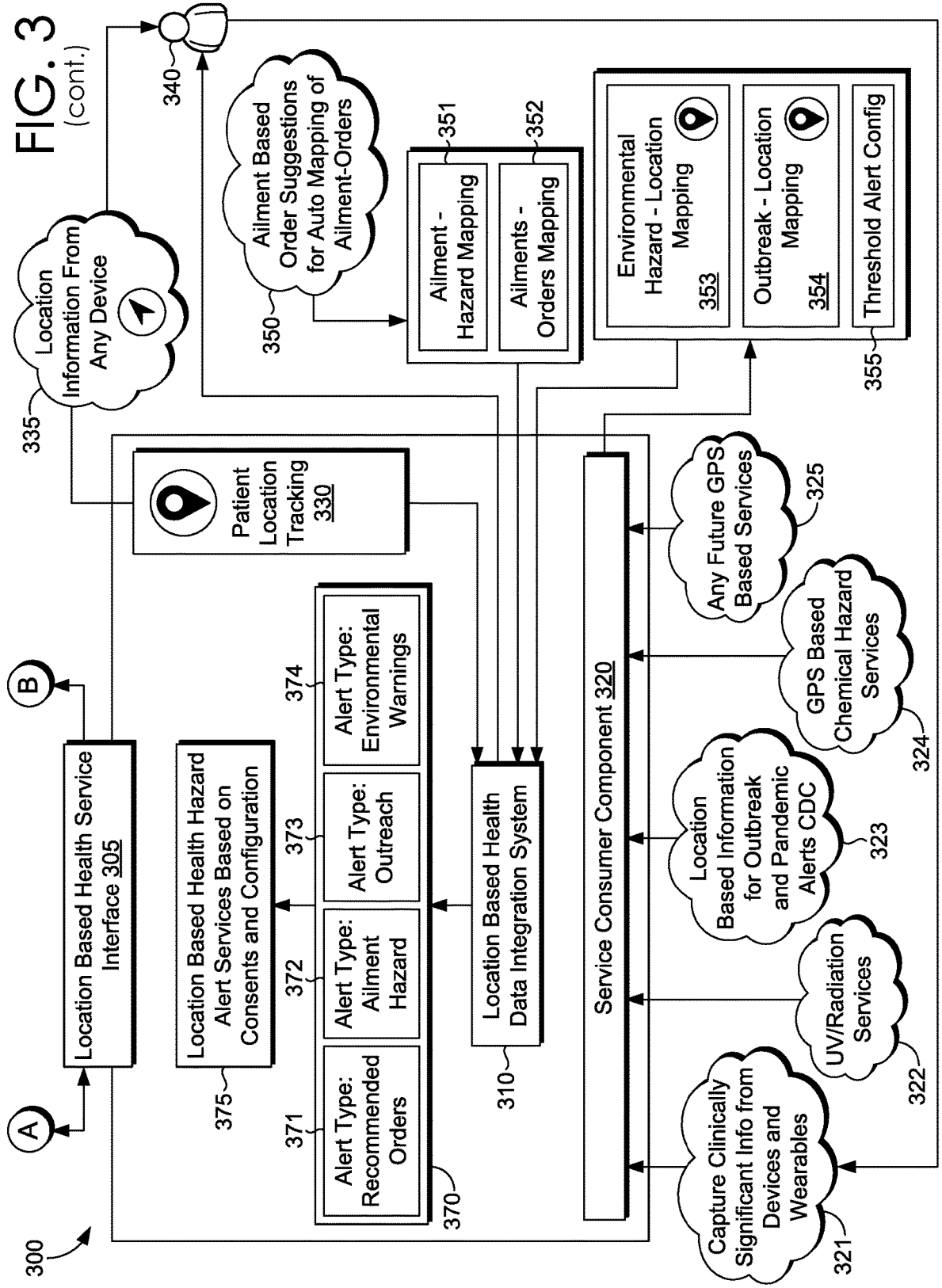

Turning now to FIG. 3, another embodiment of a location-based health system 300 is described in further detail. This embodiment comprises a location-based health service interface 305, which comprises a number of components; notably an LBHDIS 310, a service consumer component 320, a patient location tracking component 330, an alert engine 370, and a consent-based alert service 375. The location-based health service interface 305, in some embodiments, may communicate with an EMR service 315, devices and wearable 321; $3^{rd}$ party services such as 322-325; or more generally any database or service that may provide information helpful for determining a patient's exposure to a potentially hazardous condition related to a particular location or may assist a healthcare provider in providing patient healthcare.

Beginning with the LBHDIS 310, the LBHDIS 310 may receive information associated with the location of a patient 340 from a location tracking device 335. The location tracking device 335 may be any device capable of determining and transmitting location information of the patient 340. These devices are generally known and readily available, and may include mobile phones, tablets, smart watches, etc. These devices may determine location in a number of different manners, such as Bluetooth, Infrared, GPS, etc. It should be readily known to one skilled in the art that the location tracking device 335 and the method by which it determines location is not limited to the devices stated in this application and can include future location tracking systems having the ability to communicate the location of the patient 340. Additionally, information associated with the location of the patient 340 may be communicated from the location tracking device 335 to a patient location tracking component 330. The location may be monitored on a real-time basis or may be monitored intermittently. The patient location tracking component 330 may store the location information and/or may communicate the location information to the LBHDIS 310. Alternatively, in some embodiments, the location information may be directly communicated from the location tracking device 335 to the LBHDIS 310.

A service consumer component 320 may also receive information associated with the patient location, such as clinically significant information from devices or wearables 321. The clinically significant information may be any information regarding factors that contribute to an ailment or would help a medical provider in diagnosing an ailment or provide healthcare services. Some non-limiting examples of clinically significant information could be the amount of time the patient 340 is exposed to the sun; the amount of exercise the patient 340 receives; the weight gain or weight loss of the patient 340 over time; a change in the patient's body temperature, blood pressure, heart rate; etc. This information may be gathered by wearable devices. These devices may be the same the mobile devices described above. These wearable devices may also include other devices designed to capture information about the patient 340 or the patient's 340 external environmental surroundings, including external devices, such as heart-rate monitors, blood pressure monitors, air-quality monitors, UV sensors, etc. These wearable devices are not limited to external devices as described, but may include surgically implanted devices, such as pace makers, pain pumps, insulin pumps, etc. Additionally, in some embodiments, these devices may work together to communicate information about the patient 340 to the service consumer component 320. For example, an internal insulin pump might communicate via short distance communication methods to a mobile device, which might, in turn, relay the information to the service consumer component 320 via a long distance communication method.

The service consumer component 320 may also receive information about the patient's 340 surroundings from API's, for example a third-party service, such as UV radiation services, location-based information for outbreak and pandemic alerts from the Centers for Disease Control (CDC), GPS based chemical hazard services 324, and any future GPS or location-based service 325. Other examples of APIs might include weather and new reporting services. It should be understood that the number of APIs delivering information to the service consumer component 320 can be virtually unlimited and may deliver various types of location-based information.

Once information is received, in some embodiments the service consumer component 320 may communicate to a configuration and mapping system 356, which may communicate with the LBHDIS 310. The configuration and mapping system 356 may be comprised of multiple components, such as components for ailment hazard mapping 351, ailments orders mapping 352, environmental hazard location mapping 353, outbreak location mapping 354, and threshold alert configuration module 355.

The ailments hazard mapping component 351 may be a configuration system or mapping of all the ailments and its associated environmental hazards based on information received from the service consumer component 320 or other sources, including being downloaded from medical-based information sources. For example, if a person is suffering from allergy condition such as asthma, the hazards listed for this particular ailment might be pollens, dusts, air pollutions, seasonal changes, wind, temperature, altitude, etc.

The ailments order mapping component 352 may be the module which maps lists of ailments with recommended orders list 393. The mapped data can be retrieved from cloud service 350 through analytics data gathered across multiple clinics who are interested in publishing recommended orders for given ailments. For example, if a person is arriving from a location with an endemic disease or outbreak, an associated recommended list of orders required for that particular endemic disease or outbreak may be provided.

The environmental hazard location mapping component 353 may be mapped data that contains all environmental hazards associated with a given location. This data may be gathered from datasets provided by service providers to identify hazard locations. For example, the services may include UV index level, water contamination across the given location, pollen count, noxious gases, etc. The environmental hazard location mapping component 353 may also utilize an aggregate of data across multiple patients using location history and may signal that an alert is needed for others in the same location.

The outbreak location mapping component 354 may gather data from external services available today and future services, such as the APIs, patient location tracking devices and wearables, to identify endemic disease outbreak at a given location. It may also contain additional details required for more precise clinical decisions. At a higher level this module may contain mapping of outbreak diseases associated with given location as well. In one example, information from the CDC regarding a pandemic or epidemic associated with a specific area may be communicated to the outbreak location mapping component 354. In another example, the outbreak location mapping component 354 may determine a risk of an epidemic based on an aggregate of clinically signification information from devices and wearables 321 across many patients in a particular region that may have similar changes in clinically significant information.

The threshold alert configuration module 355 may contain configuration data associated with individual hazards. The threshold value defines what level of exposure and the duration of that exposure that may constitute a hazard to the person.

Turning back now to the LBHDIS 310 part of the location-based health service interface 305, the LBHDIS 310 may communicate with an alert engine 370. The alert engine 370, may be the part of the system that comprises well-defined rules and categories of various alerts generated from LBHDIS 310. The alert engine 370 may be responsible for sending alert data to reporting services through which many entities consume services, such as person, EMR, physician, hospital, pharmacy etc. The alert engine 370 may contain further categories of information, such as, recommendation orders 371, ailment hazard 372, outbreak information 373, and/or environmental warnings 374. For example, the alert recommendation orders 371 may be the part of alert system that is responsible for gathering enough information to ensure that it provides a list of recommended orders gathered from configuration and mapping 350-355 to the EMR service 315 for accurate clinical decision support and support physician diagnosis decisions. A real-world example might be: if a person is visiting hospital after her travel to a location where an Ebola outbreak has occurred. The data will be captured by the LBHDIS 310 during the person's visit based on the location tracking of the person. Subsequently, a recommended list of orders may be generated and suggested to physician based on the person's consents.

The alert engine 370 may also contain an ailment hazard component 372. The ailment hazard component 372 may be responsible for sending alerts based on a location hazard that can trigger or aggravate the conditions within the patient 340. For example, the patient 340 may have asthma. Based on information received by APIs 322-325 and delivered to the LBHDIS 310, the pollen count of the particular location may be high enough to aggravate the symptoms of the asthmatic. Thus, an alert may be generated and communicated to the patient 340 or another, based on consents, that the pollen count is too high. In another embodiment, an alert or suggestion may communicate to the patient 340 that preventative medications should be increased to avoid having to use a rescue inhaler.

Further, the alert engine 370 may comprise an outbreak alert component 373. This component may be responsible for generating an alert to persons within a specific area that an epidemic may be associated with a particular area. The alert might suggest that persons move to another area that is not associated with the outbreak and may recommend moving to an area where the hazard has not occurred. Similarly, the alert engine 370 may contain an alert type or component for environmental warnings 374. Like the outbreak alert component 373, the environmental warning component 374 may communicate an alert based on environmental factors, such as pollens, water pollution, air pollution, noxious gas contamination, or UV exposure, or other environmental factors that may pose potential harm to a patient. The environmental warning component 374 may communicate or suggest that persons move to another area that is not associated with the environmental hazard and may recommend moving to safer area, such as indoors.

The alert engine 370 may also communicate with patient consent configurations on the consent-based alert service 375 to ensure the alert messages are sent to respective entities based on the consent configuration. For example, the patient 340 may consent to having the location information delivered to a primary care physician when the patient location is associated with an outbreak.

Turning now to the EMR service 315, which may be in communication with the location-based health service interface 305, the EMR service 315, in some embodiments, may comprise an EMR database 385. The EMR database 385 may store or be in communication with another database that stores information related to a person's consent configuration 388, sequencing data and threshold configuration 386, patient ailments data 387, genomic sequencing data 389 that may be provided by genomic sequencing services 390, and other information, such as location base hazard trends 391, patient exposed hazard location 392, recommended orders list 393, and endemic/pandemic outbreak location 394.

The sequencing data and threshold configuration 386 may provide a mechanism to get a patient's complete sequencing data and, based on the analysis, may provide predictable variants data along with threshold percentages. The medical provider or the system may help in identifying each of the predictable conditions with higher threshold, and may help to store it as part of a patient ailment record 387. The patient ailment record 387 may store information collected by the EMR service 315, including all the ailments associated with the patient 340 and hold this information for future analyses.

Similarly, the EMR database 315 may store or communicate with another database that stores the person consent configuration 388. The patient may choose to personalize the consent information so as to maintain privacy. The patient may choose to have alerts sent only to the patient, or choose to have the alerts sent to a primary care physician, or another physician of the patient's choosing. More generally, the patient may personalize how the medical information is to be distributed in any fashion. Accordingly, the patient may also consent to have their location monitored but may not allow that location information to be shared; instead, only allowing exposure information to be shared with others of the patient's choosing. Alternatively, the patient may alter the consent configurations such that information is only shared with others when exposures to hazards create a certain threshold of risk to the patient.

The EMR service 315 may also include genomic sequencing data 389. The genomic sequencing data 389 may be stored or received from a genomic sequencing service 390. The genomic sequencing data 389 may be one of various types of patient-specific information that is housed or retrieved by the EMR service 315. Patient-specific data, such as this, may be used by the location-based health service interface 305 to determine that a particular individual may be at a higher risk or predisposition to certain ailments, and may determine an alert is necessary based on information received from the service consumer component 320, the location tracking device 335 and/or the configuration and mapping system 356, described above. Once an alert is determined, the alert may be communicated via an alert service 380, which may be in communication with the location-based health service interface 305 and/or the EMR service 315. The alert may be communicated to any person or entity based on the patient consent configurations 388. These include, but are not limited to, physicians, care providers, insurers, hospitals, emergency department, etc. The location-based health service interface 305 and/or the EMR service 315 may be a computing system such as that described in FIG. 1.

Figure 4:
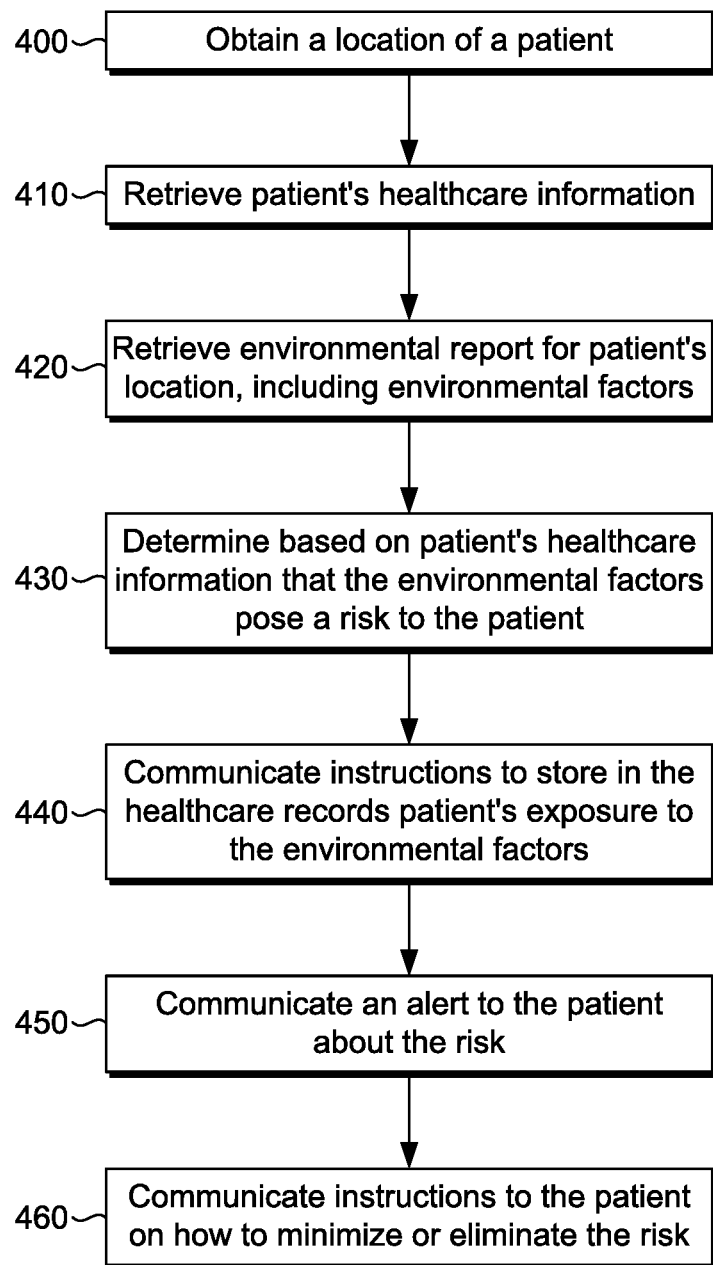
FIG. 4 is a flow chart of an exemplary method for retrieving and storing a patient's location information in association with the patient's healthcare information.

FIG. 4 depicts one embodiment of a computerized method for utilizing an embodiment of a location-based healthcare system, such as the two exemplary embodiments described in FIGS. 2-3. For example, a general computer, such as that described by the computing environment in FIG. 1, may be contain computer-executable instructions embodied that execute a method for improving medical records of an individual or patient based on location-specific risks posed to the patient. In step 400 of FIG. 4, the computer may be instructed to obtain from a mobile device the location of a patient. Alternatively, in another embodiment, the computer may receive information associated with a patient's location, which may then prompt the computer to continue with step 410.

In step 410 of the exemplary method of FIG. 4, the computer retrieves from a database, the medical records or health information of the patient. As seen in the embodiment of FIG. 3, this step may be performed when the location-based health service interface 305 retrieves the medical records or health-related information of the patient from the EMR service 315. Similarly, in step 420 of FIG. 4, the method may comprise retrieving from a service provider an environmental report for the location of the patient. The service provider may be the APIs previously discusses, e.g., a third party that may deliver reports about environmental conditions or factors, such as pollen count, UV index, city pollution reports, etc.

Step 430 of FIG. 4 may comprise determining, based on the medical records or information of the patient, that the patient's exposure to certain environmental conditions or factors at the patient's location may pose a risk to the patient. The risk may be the type of risk that would affect all persons in the area, such as a viral outbreak. Alternatively, it may pose a patient-specific risk, such as a UV index that is too high for a patient currently undergoing chemotherapy to be outside for an extended amount of time. In some embodiments, a patient-specific risk may be predefined in the medical records. In other embodiments, the patient-specific risk may be determined by a location-based service interface that associates certain diagnoses with certain risks, such as determining from the medical records that a patient has asthma and associated a risk of exposure to a particular environmental pollen level.

Under step 440, the medical records for the patient may be improved by having the location-based service interface communicate with the EMR service that a patient has been exposed to a patient specific risk, such as that determined by step 430, and instructing the EMR service to store the information associated with the patient for future access, e.g., by a physician, a hospital, an insurance company, or the patient.

In some embodiments an additional step of communicating an alert to the patient may be provided, such as step 450 of FIG. 4. The alert may be in any form that signals to the patient that a patient-specific risk might be present. Some examples of alerts might include text messages, emails, phone calls, social media status changes, etc. Additionally, the alert may also be provided to other entities, such as hospitals in the surrounding area, primary care physicians, first-responder authorities, patient-specified emergency contacts, etc. The patient may preselect the desired recipients of alerts and this data may be stored in a component of an alert engine associated with an embodiment of a location-based health service interface.

In other embodiments, the alert may communicate a suggestion or instructions to the patient, such as the represented by step 460 of FIG. 4. The instructions communicated to the patient may be instructions to reduce or eliminate the patient-specific risk. For example, it may be determined that a patient with sensitivity to UV radiation is outdoors. A certain amount of UV radiation exposure to the patient may not be harmful; however, after a certain threshold is reached, the patient may suffer negative effects from the exposure. Having determined, such as from an API described previously, the level or index of UV radiation for a given area, a location-based health service interface, or a component of the location-based health service interface, may determine the amount of time the patient may spend outdoors in a certain area before reaching the threshold level of sun exposure that is safe for the patient. Once the patient reaches the threshold level, the system may send an alert with instructions to move from the outdoor location to an indoor location where UV exposure would be reduced or eliminated.

Figure 5:
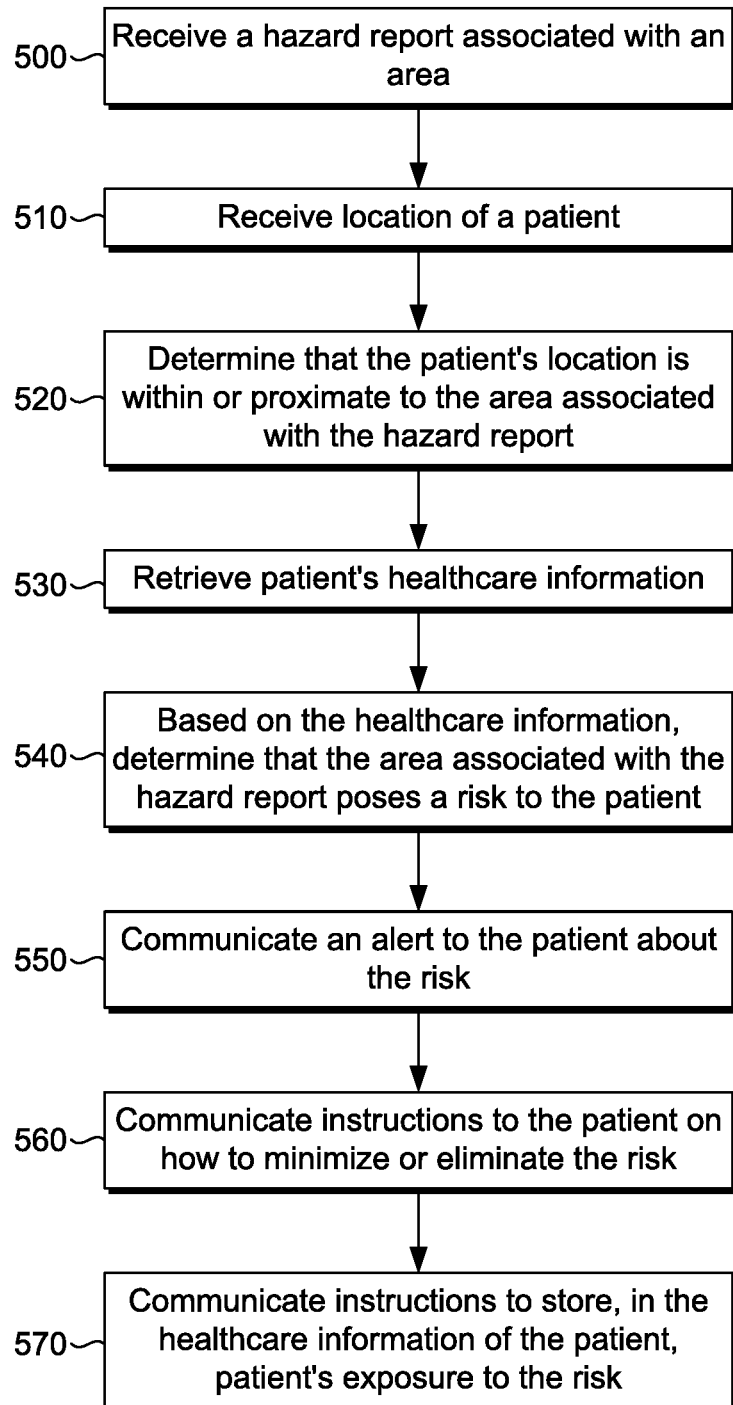
FIG. 5 is a flow chart of an exemplary method for communicating an alert to a patient based on a location-specific risk to the patient.

In another embodiment, the computerized method performed by a location-based health service interface may be similar to that described by FIG. 5. In step 500, the location-based health service interface may receive a hazard report associated with an area. For example, the hazard report may be received from an API, as described above. The hazard report may be associated with any environmental hazard, occupational hazard, or man-made hazard that may pose a health threat to persons in the area. For example, the hazard may be an allergen, a dangerous ultraviolet index, a dangerous air pollution index, a bacterial outbreak, a viral outbreak, a fungal outbreak, an algal bloom, a chemical spill, a contaminated water alert, a radiation or radioactivity increase, and so on. A hazard report may be associated with any activity or event that may pose a threat to human health or safety, whether the activity affects all persons in the area or whether the activity increases the health risks of only persons in the area with sensitivity to a particular hazard or activity.

In step 510, the health service interface may receive a location of a patient. As described above in greater detail, the location of a patient may be sent to the interface from a mobile device capable of determining location. Additionally, the interface may receive health information related to the patient's measureable outcome data from patient wearables, such as heart rate, oxygen stats, blood pressure, sugar level, etc.

In step 520 of the exemplary method, the health service interface may determine that the patient's location is within or is proximate to the area associated with the hazard report or event. For example, if the interface receives a report that a certain geographical county is experiencing a hazard associated with an oil or chemical spill, this could be hazardous to patients that are exposed. The interface may determine that certain patients are located within the county experiencing the hazard and may also determine that other patients are located within counties surrounding the county experiencing the hazard. In other embodiments, it may determine that patients are within a certain distance surrounding the hazard location. In yet other embodiments, the location distances for determining what patients are proximate to the hazardous event may be predefined based on the type of hazard, or may be determined by the integration system as aggregate data of multiple patients is received, such as detecting the spread of a contagion.

In step 530, the interface may retrieve the healthcare records associated with the patients that are within or proximate to the area associated with the hazard. The healthcare records may be retrieved from an EMR system.

In step 540, the interface may determine that the hazard poses a health-related or medical-related risk to the patients within or proximate to the area. For example, the hazard associated with the area may be an abnormally high pollen count. Based on the health records of the patients in or around the area, the interface may determine that patients with, for example, a diagnosis of asthma; a history of lung conditions or cancer; or temporarily conditions, such as the flu or bronchitis, are at risk of aggravating their individual ailments.

Based on determining that a patient might suffer a health-related risk, the interface, via an alert engine, might send an alert notification to a patient. The alert may be in any form that communicates to the patient that they might be exposed to a hazard posing a health-related risk or they might have the potential to be exposed to a hazard posing a health-related risk if they enter a certain area.

In some embodiments, the method may also comprise step 560, communicating instructions to the patient on how to reduce or eliminate the risk. For example, patients suffering from allergies might be exposed to a pollen count that breaches the safety threshold for that particular patient. The system may be able to, based on the healthcare records, suggest the patient increase preventative medication in order to reduce the chance of a server allergic reaction that may require the use of a rescue inhaler or medical care.

In some embodiments, the method may also comprise communicating instructions to an EMR system to store information about the patient's location and exposure to health risks. The information may be associated with the patient in the patient's electronic medical record so that it may later be accessed by other entities, such as a primary care physician, an emergency department of a hospital, an insurance company, etc.

In some embodiments, the system might recommend to a physician specific orders for a particular patient based on the patient's location and the patient's exposure to a health-related risk. For example, a patient might be suffering from a location-based, health-related risk that causes the patient not to be able to communicate symptoms to an emergency department physician. The physician may be able to access the medical records of the patient and determine that the patient was at a particular location and exposed to a particular risk. The interface may associate certain treatments with the risk. The interface may recommend orders associated with the treatments to the physician. A real-world example might be determining that a patient was in an area associated with an epidemic or outbreak of a particular contagion. The interface may provide information to a treating medical provider that the patient was in the area associate with a contagion. It may further recommend orders for the treatments associated with the contagion. Even if the patient was not able to communicate to the provider, maybe because of unconsciousness, their location information, the interface may be able to communicate this for them as it would have stored this information on the EMR database or system.

Figure 6:
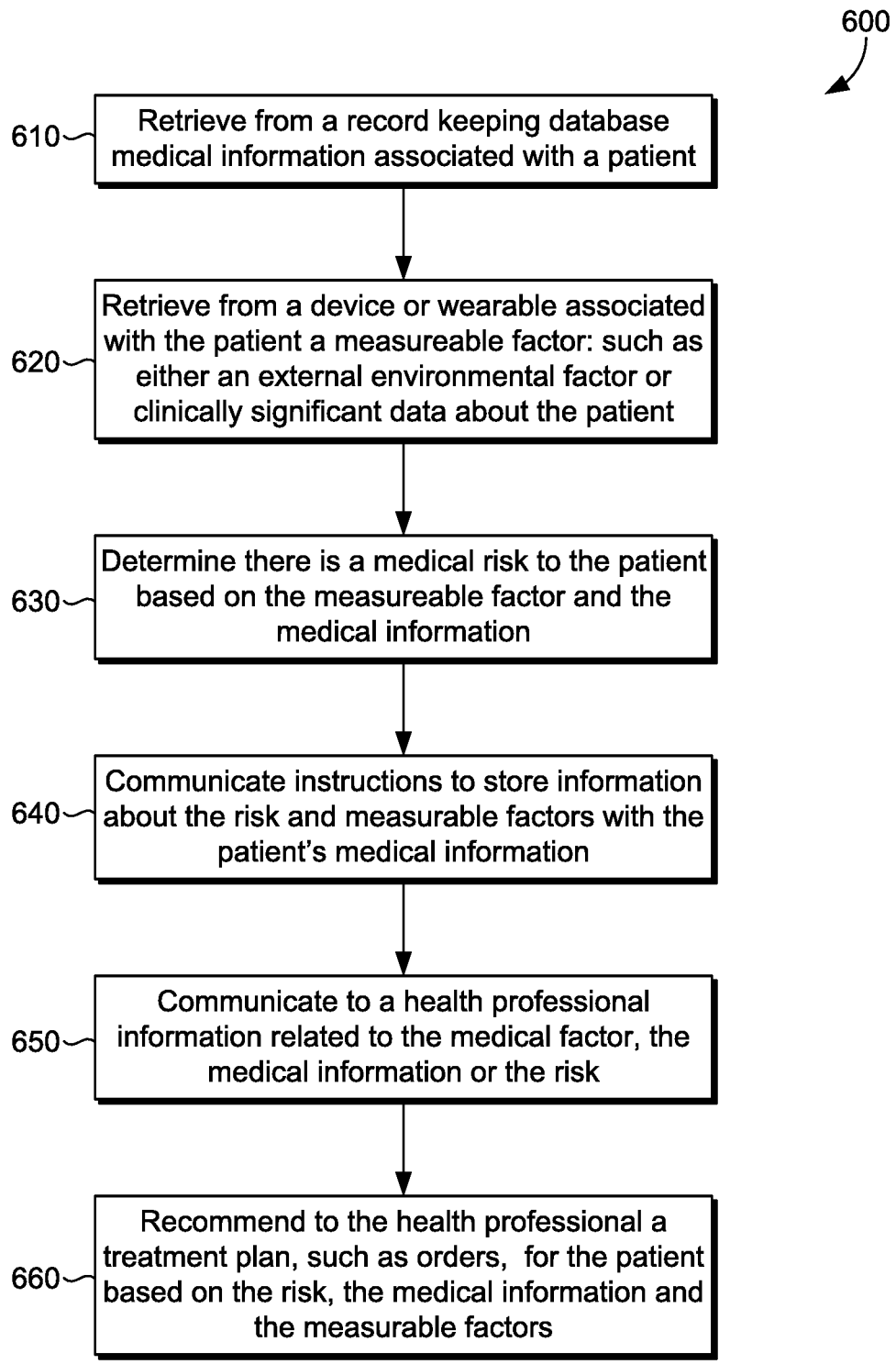
FIG. 6 is a flow chart of an exemplary method for determining a medical risk to a patient based on information received from a device or wearable.

Turning now to FIG. 6, another embodiment is represented by method 600. In step 610, medical information associated with a patient is received by a system, such as that presented by FIG. 1. The medical information may be the patient's EMR and the database on which it is store may be in one location or the EMRs may be an aggregate of patient information that is stored across multiple databases. The EMR may contain diagnoses of patient ailments. And the EMRs may also contain a list or set of conditions or measurable factors that may aggravate prior conditions or may cause new conditions, ailments, or symptoms.

In step 620 of method 600, a measurable factor is retrieved from a device or a wearable associated with the patient. For example the devices or wearables may be any device capable of measuring a clinically significant factor of the patient or may measure anything in the environmental surroundings of the patient. For example, some devices may be internal, such as insulin pumps, pace makers, or cardiac defibrillators. Other communication-enabled, implanted medical devices may be considered as well. Other types of wearable devices associated with the patient may measure clinically significant information as well. For instance, a patient may wear a device capable of monitoring the patient's oxygen status, internal temperature, heart rate, blood pressure, breathing rate, etc. Other non-wearables devices that may communicate clinically significant information can be utilized, such as glucose meters, scales for measuring patient weight, nebulizers, etc. In other embodiments the device or wearable may monitor a patient's external surroundings. For example, some external surroundings that may be monitored are environmental temperature, whether the patient is indoors or outdoors, the amount of UV light, air quality, etc. Further, all of these may be their own independent device or wearable unit, or they may be app enabled, for example causing a mobile phone to monitor this information.

In step 630, it is determined whether the measurable factor poses a risk to the patient. In some embodiments, the health risk may be specific to the individual patient based on their health records, while in other embodiments, it may be a general risk to all patients. For example, a device or wearable associated with the patient may monitor the air quality in the patient's environment. Based on the patient's medical records, the system may determine that the patient recently had bronchitis or pneumonia, or may have a history of poor pulmonary function, such as that caused by Chronic Obstructed Pulmonary Disease or Cystic Fibrosis. Because of this, the patient may be sensitive to air pollution levels or high pollen levels. Based on the medical records, a threshold of air quality may be obtained or determined. Once the air quality breaches the threshold for that patient, the system may determine that this is a medical risk to the patient. In some embodiments, the medical risk may be alerted to the patient by the alert engine or others of the patient's choosing, such as per their consent configurations. In some instances, the alert may be communicated to a medical professional, such as the patient's doctor or an emergency room physician. In these cases, the system may provide or recommend a plan of care or orders to the medical professional based on the medical records and the risk. The alert to the patient may include instructions to begin or alter preventative medications, such as increasing a dosage of a certain medication based on information received from the device or wearable. This information may come from standing orders listed in the patient's medical history or from a list of orders associated with particular measurable factors or risks. In other embodiments, the threshold level may be dangerous to all persons. For example, the system may contain a standard or default threshold for air quality. If the device or wearable determines the air quality has breached this threshold, then the alerts or instructions may be sent.

At step 640, the system may communicate instructions to store information about the risk and/or the measurable factors in the patient's EMR. In an embodiment, the system may determine that clinically significant information or environmental information may not constitute a risk at the preset moment; however, prolonged exposure to these factors may create a risk. Therefore, this type of information may be stored in the patient's medical records without alerting the patient in the present. This information may later be accessed during the retrieving step 610 to help determine whether there is a medical risk to the patient. For example, the patient may be outside and exposed to UV light. A low amount may not pose a risk to the patient. But the amount of time the patient is exposed may be stored in the EMR, anyway. At a later time, the patient may be again exposed to UV light outside. During the retrieving step 610, the system may find information related to the prior exposure, and during the determining step 630, may determine that the prior exposure combined with the current measurable amount of UV light has breached the threshold and poses a risk to the patient.

In some embodiments, the alert engine may perform the step of communicating to a health professional information related to the measureable factor, the patient's medical information, and/or the risk, such as step 650 in method 600. The consent configurations set by the patient may provide the instructions for which professional the system should communicate the information. In some embodiments, the system may recommend to a health professional a treatment plan, such as orders, for the patient based on the combined information of the EMRs, the measurable factors, and the risks. The orders may be predetermined and stored in the patient's EMR to be ordered for the patient if certain measurable factors are determined. Alternatively, in other embodiments, a list of orders may be associated with certain ailments or with exposure to certain measureable factors. Upon measuring or detecting these measurable factors, the system may associate the list of orders with the measurable factors and generate a recommendation to the healthcare professional.

Figure 7:
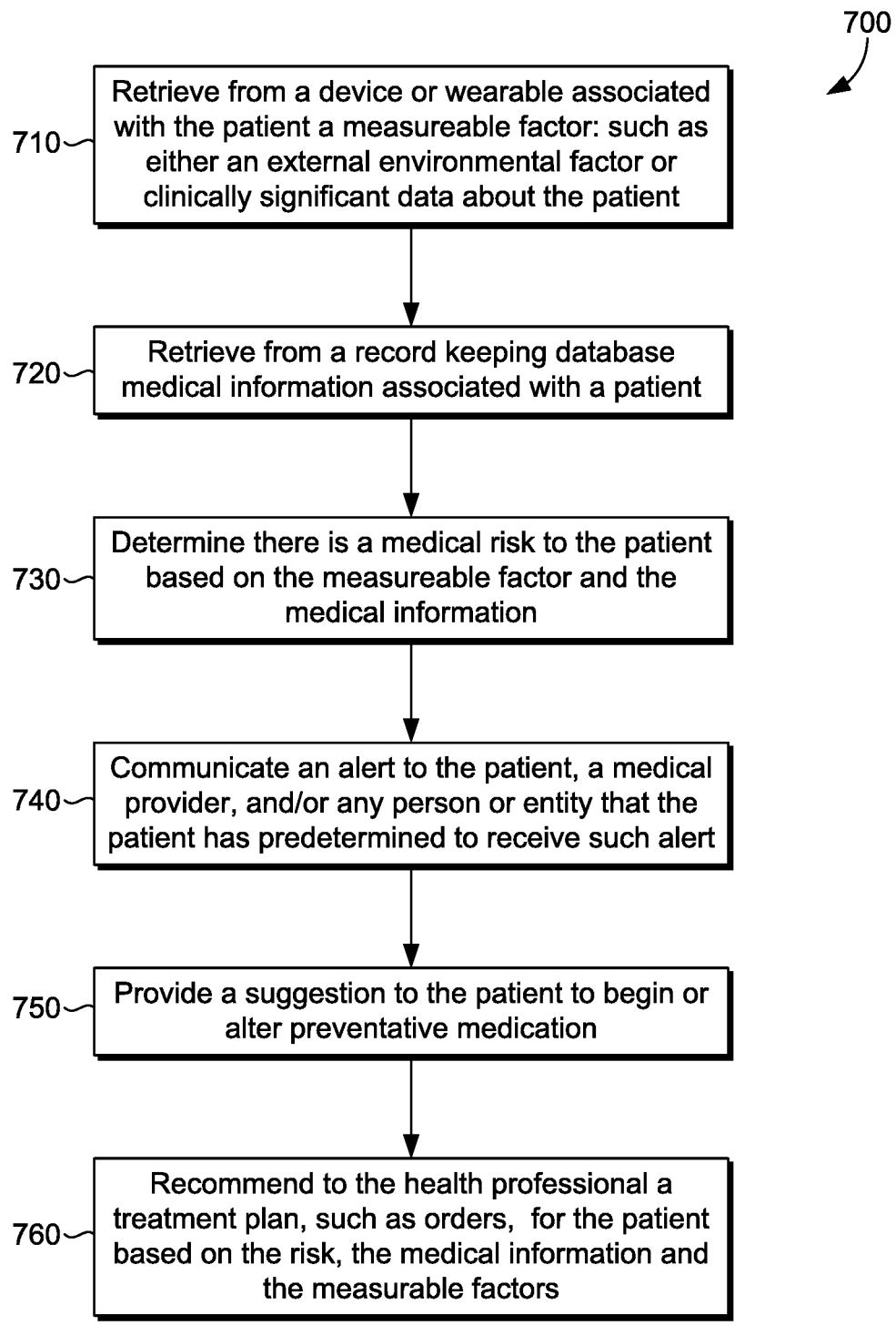
FIG. 7 is a flow chart of an exemplary method for alerting a patient of a medical risk based on information received from a device or wearable.

Another embodiment of the healthcare system based on devices or wearables is represented by the exemplary method 700 in FIG. 7. In step 710, a measureable factor is retrieved from a device or wearable associated with the patient. In step 720, medical information associated with the patient is retrieve from a record-keeping database. In step 730, the system determines whether there is a medical risk to the patient based on the measurable factor and/or the medical information. In step 740, an alert is communicated to the patient or others that are predetermined by the patient to receive such alerts. The alert may contain information associated with the risk and the measurable factor. In some embodiments, step 750 may provide a suggestion to the patient to begin or alter preventative medication. This may be communicated with the alert, or this information may be communicated separately. In other embodiments, this information may be communicated at the request of the patient. In some embodiments, method 700 may also comprise step 760. In step 760, a treatment plan and/or orders for the patient are recommended to a health professional based on the risk, the medical information, and the measurable factors. The steps in method 700 may also be similar to some of those described in other embodiments.

Figure 8:
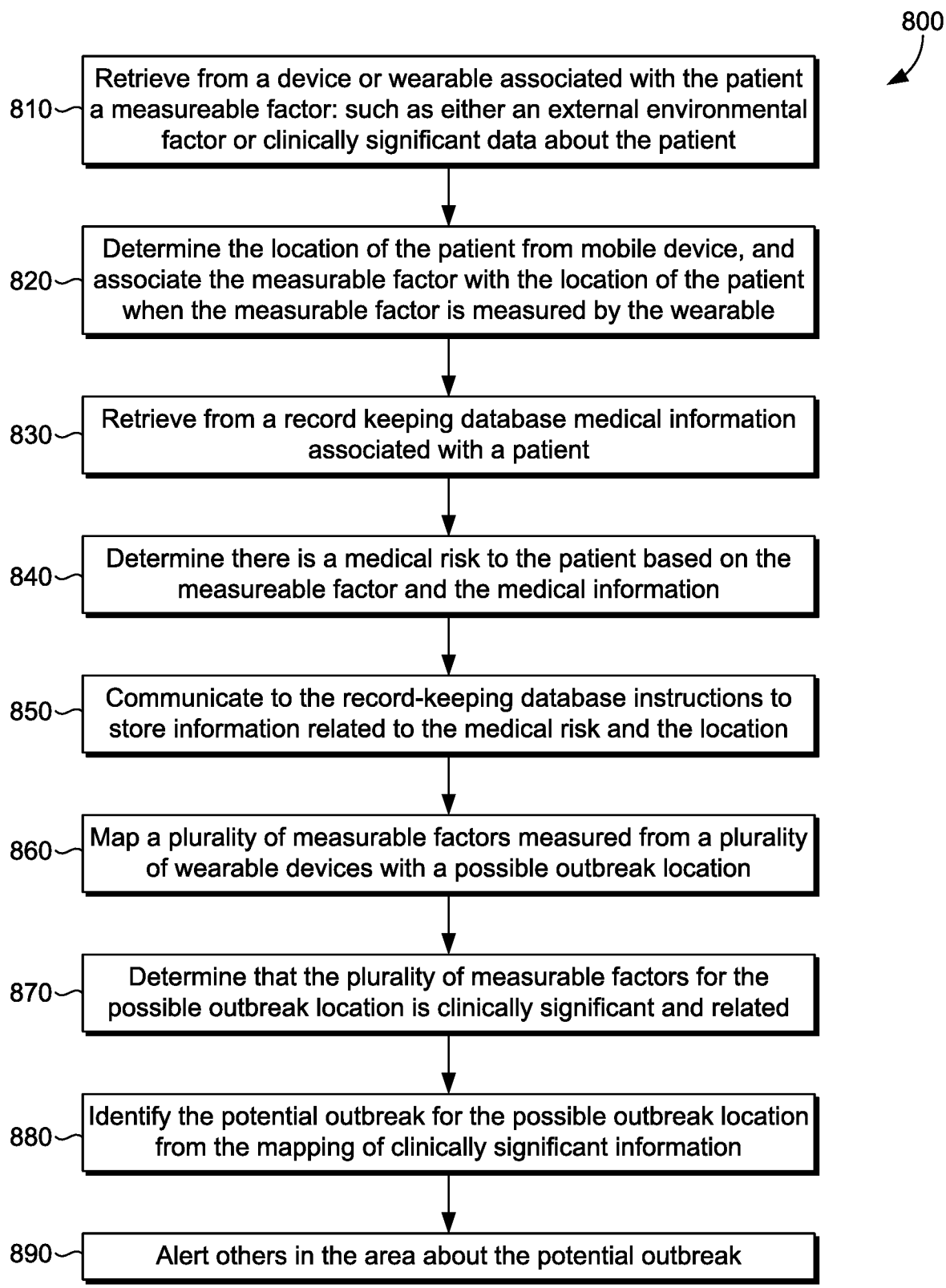
FIG. 8 is a flow chart of an exemplary method for associating a location with a medical risk to a patient based on information received from a device or wearable.

In another embodiment, the systems as previously described may perform method 800, represented in FIG. 8. In step 810, a measurable factor may be retrieved from a device or wearable associated with the patient. In step 820 the location of the patient may be determined by a mobile device associated with the patient. The measurable factor may be associated with the location in which it was measured. For example, if a device or wearable detects poor air quality, the location of the patient may be determined so that the system may associate the poor air quality in that particular location. In other embodiments, the device or wearable may determine a clinically significant event/factor occurring with the patient. This event may also be associated with the patient's location when it was measured. It may also be associated with historical patient locations, such as where the patient has been over a predetermined time frame. For example, it may be associated with multiple locations of the patient over the last 48 hours.

In step 830, medical information associated with the patient may be retrieved from a record-keeping database. In step 840, the system may determine that there is a medical risk to the patient based on the measurable factors and the medical information. In step 850, the system may communicate to the record-keeping database instructions to store the information related to the medical risk and the location. In some embodiments, the information is stored in association with the patient, such as on the patient's EMR. In some embodiments, the information may be stored on another database, where the information is stored in association with the measureable factors or the location. This would allow for mapping multiple measurable factors measured from multiple devices and wearables, such as described by step 860. For instance, accessing this information may allow someone to determine all the measurable factors that were measured for a particular location. Similarly, a person may access the data by determining all the locations for which certain measurable factors have been measured. Spikes in measurable factors above a predetermined threshold or above typical baseline may indicate a potential outbreak, as described by step 870. The system may further identify the potential outbreak from the mapped data, as described by step 880. And may also, in step 890, alert others in the area of the potential outbreak or may alert third parties, such as the CDC. Additionally, some of these steps in method 800 may also be similar to those described in other embodiments.

Other embodiments generally relate to media, systems, and methods for various embodiments of a location-based healthcare system. In one embodiment, a computerized method for improving medical records of an individual is presented. The method of this embodiment comprises: obtaining from a mobile device a location of the individual; retrieving from a record-keeping database medical-related information associated with the individual; retrieving from a service provider an environmental report for the location of the individual, wherein the environmental report comprises one or more environmental factors; determining, based on the medical-related information associated with the individual, that an exposure to the environmental factor poses a medical risk; and based on determining the medical risk, communicating instructions to the record-keeping database to store, in association with the individual, information related to the exposure to the environmental factor.

In another embodiment, a computerized method for communicating an alert to an individual of a medical-related risk is presented. In this embodiment, the method comprises: receiving a hazard report from a service provider, wherein the hazard report is associated with an area; retrieving an individual-specific location from a mobile device associated with the individual; determining that the individual-specific location is within or proximate to the area associated with the hazard report; retrieving from a record-keeping database a medical-related information associated with the individual; based at least in part on the medical-related information associated with the individual and the hazard report, determining that the area poses the medical-related risk to the individual; and communicating the alert to the individual of the medical-related risk associated with the area.

From the foregoing, it will be seen that this disclosure is well adapted to attain all the ends and objects described above with other advantages that are obvious and inherent to the structure. It will be understood that certain features and subcombinations are of utility and may be employed without reference to other features and subcombinations. This is contemplated by and is within the scope of the claims. Since many possible embodiments may be made of the without departing from the scope, it is to be understood that all matter in this application is to be interpreted as illustrative and not in a limiting sense.

What is claimed is:

1. One or more non-transitory computer storage media having computer-executable instructions embodied thereon that, when executed, perform a method for improving medical records of an individual based on received information from a device, the method comprising:
retrieving from a record-keeping database medical-related information comprising a predisposition unique to the individual to certain ailments linked with a measurable factor associated with the individual;
retrieving from a device associated with the individual the measurable factor comprising a measurable outcome data from the device;
determining, utilizing a computer processor, a location of the individual from location information received from a mobile device, and associating the measurable factor with the location of the individual when the measurable factor is measured by a wearable, based at least in part on the medical-related information and the measurable factor, that the measurable factor poses a medical risk to the individual based on the predisposition unique to the individual linked with the measurable factor; and
converting, utilizing a computer processor, the measurable factor measured by the wearable to a standardized format as updated information about the individual;
communicating instructions to the record-keeping database to store, in association with the individual, the measurable factor measured by the wearable in the standardized format related to the medical risk.

2. The media of claim 1, further comprising the step of communicating to a medical provider that the individual was exposed to the medical risk.

3. The media of claim 2, further comprising the step of recommending an order to the medical provider for the individual, wherein the order is selected from a list of orders, the list of orders being associated with the medical risk.

4. The media of claim 1, wherein the device is a wearable device associated with the individual.

5. One or more non-transitory computer storage media having computer-executable instructions embodied thereon that, when executed, perform a method for communicating an alert to a recipient of a medical risk, the method comprising:
retrieving from a device associated with an individual a measurable factor;
retrieving from a record-keeping database medical-related information comprising a predisposition unique to the individual to certain ailments linked with a measurable factor associated with the individual;
determining, utilizing a computer processor, a location of the individual from location information received from a mobile device, and associating the measurable factor with the location of the individual when the measurable factor is measured by a wearable, based at least in part on the medical-related information, that the measurable factor poses a medical risk to the individual based on the predisposition unique to the individual linked with the measurable factor;
converting, utilizing a computer processor, the measurable factor measured by the wearable to a standardized format as updated information about the individual;
converting, utilizing a computer processor, the measurable factor measured by the wearable to a standardized format as updated information about the individual;

communicating instructions to the record-keeping database to store, in association with the individual, the measurable factor measured by the wearable in the standardized format related to the medical risk; and
communicating an alert to the recipient regarding the medical risk.

6. The media of claim 5, wherein the recipient is the individual.

7. The media of claim 6, wherein the alert comprises a suggestion, the suggestion comprising instructions for the individual to begin or alter a preventative medication.

8. The media of claim 5, further comprising the steps of determining a first location of the individual from a mobile device associated with the individual and configured to monitor the location of the individual, and associating the first location with the medical risk, and communicating instructions to the individual to move from the first location to a second location, wherein the second location reduces or eliminates exposure of the individual to the medical risk as determined by the device.

9. The media of claim 5, wherein the recipient comprises one or more recipients that have been predetermined by the individual to receive the alert.

10. The media of claim 5, wherein the recipient is a medical provider.

11. The media of claim 10, further comprising the step of recommending an order to the medical provider for the individual.

12. The media of claim 11, wherein the order is selected from a list of orders, the list of orders being associated with medical risk.

13. The media of claim 5, wherein the measurable factor is an external environmental factor.

14. The media of claim 5, wherein the measurable factor is clinically significant information regarding factors contributing to the certain ailment associated with the individual.

15. A computerized system comprising:
a mobile device configured to monitor the location of an individual;
a wearable device associated with the individual;
one or more processors; and
computer storage memory having computer-executable instructions stored thereon which, when executed by the processor, implement a method for tracking location exposure of the individual to factors that cause a medical risk to the individual based on a predisposition unique to the individual and linked with a measurable factor, the method comprising:
receiving from the wearable device a measurable factor comprising a measurable outcome data from the device;
determining, utilizing a computer processor, the location of the individual from location information received from the mobile device, and associating the measurable factor with the location of the individual when the measurable factor is measured by the wearable;
retrieving, from a record-keeping database, medical-related information comprising the predisposition unique to the individual to certain ailments linked with a measurable factor associated with the individual;
determining, based at least partly on the medical-related information and the measurable factor, that the location poses a medical risk to the individual based on the predisposition unique to the individual linked with the measurable factor;
converting, utilizing a computer processor, the measurable factor measured by the wearable to a standardized format as updated information about the individual; and
communicating to the record-keeping database instructions to store in association with the individual, the measurable factor measured by the wearable in the standardized format related to the medical risk and the location.

16. The system of claim 5, further comprising the step of identifying a potential outbreak, the step of identifying a potential outbreak comprising:
mapping a plurality of measurable factors measured from a plurality of wearable devices with a possible outbreak location;
determining that the plurality of measurable factors for the possible outbreak location is clinically significant and related; and
identifying the potential outbreak for the possible outbreak location from the mapping of clinically significant information.

17. The system of claim 16, further comprising the step of communicating an alert to other individuals within or proximate to the possible outbreak location, the alert based on the potential outbreak.

18. The system of claim 15, wherein the mobile device and the wearable device are the same.

19. The system of claim 15, wherein the mobile device and the wearable device are in communication.

* * * * *